United States Patent [19]

Mills et al.

[11] Patent Number: 4,959,475

[45] Date of Patent: Sep. 25, 1990

[54] PROCESS FOR THE PRODUCTION OF 2,4-DIAMINO-6-PIPERIDINYL-PYRIMI-DINE-3-N-OXIDE

[75] Inventors: Lester Mills, Naters; Hans P. Mettler, Brig-Glis; Felix Previdoli, Brig; Francois Moulin, Neuchâtel, all of Switzerland

[73] Assignee: Lonza Ltd., Gampel/Valais, Switzerland

[21] Appl. No.: 458,292

[22] Filed: Dec. 28, 1989

[30] Foreign Application Priority Data

Jan. 4, 1989 [CH] Switzerland .............................. 20/89

[51] Int. Cl.$^5$ ........................................... C07D 401/04
[52] U.S. Cl. ..................................................... 544/324
[58] Field of Search ........................................ 544/324

[56] References Cited

U.S. PATENT DOCUMENTS 3,644,364  2/1972  Anthony .............................. 544/324

FOREIGN PATENT DOCUMENTS 0252515  1/1988  European Pat. Off. .
0254148  1/1988  European Pat. Off. .
4011706  12/1970  Japan ................................. 544/324

OTHER PUBLICATIONS

Vito M. Campese, "Minoxidil: A Review of its Pharmacological Properties and Therapeutic Use," Drugs, vol. 22, pp. 257 to 278, (1981).
J. M. McCall, "A New Approach to Triaminopyrimidine N-Oxides", Jnl. of Org. Chem., vol. 40, No. 22, Oct. 1975, pp. 3304 to 3307.
Pharm. Ind. 46, (1984), pp. 937 to 938.
Pharm. Ind. 47, (1985), p. 506.
Merck Index, 10th edition, 6069 Minoxidil.

*Primary Examiner*—Cecilia Shen
*Attorney, Agent, or Firm*—Fisher, Christen & Sabol

[57] ABSTRACT

Process for the production of 2,4-diamino-6-piperidinyl-pyridine-3-N-oxide starting from hydroxylamine and cyanamide by way of intermediate product 2,4-diamino-6-hydroxypyrimidine-3-N-oxide.

14 Claims, No Drawings

PROCESS FOR THE PRODUCTION OF 2,4-DIAMINO-6-PIPERIDINYL-PYRIMIDINE-3-N-OXIDE

BACKGROUND OF THE INVENTION

1. Field Of The Invention

The invention relates to a process for the production of 2,4-diamino-6-piperidinylpyrimidine-3-N-oxide (Minoxidil).

2. Background Art

Minoxidil is characterized by an excellent antihypertensive effect [Drugs, 22 (1981), 257] and is known in many countries as an antihypertensive agent. Recently, the use of the compound for therapeutic cosmetic increasingly comes to the fore, since applied externally in dilute solution it effectively stimulates hair growth [Pharm. Ind., 46, (1984), 937, and Pharm. Ind., 47, (1985), 506]. In the technical literature the designation Minoxidil has two meanings since it can be in two tautomeric forms. In Chemical Abstracts the compound was mentioned before 1972 under the name 6-amino-1,2-dihydro-1-hydroxy-2-imino-4-piperidinopyrimidine, while after that date it was referred to under the designation 6-(1-piperidinyl)-2,4-pyrimidinediamine-3-oxide. Several processes are known for the production of Minoxidil. One process starts from 2,6-diamino-4-chloropyridimine. By oxidation with, e.g., chloroperbenzoic acid or hydrogen peroxide, the corresponding N-oxides are produced, which are then further reacted (European Published Patent Application No. 0254158). Another known process starts from 2-iminopyrimidine derivatives containing acyl and/or acyloxy groups, e.g., from 6-amino-1,2-dihydro-1-acetoxy-2-imino-4-chloropyrimidine. By reaction with piperidine, the corresponding piperidino compound is produced which is then hydrolyzed (European Published Patent Application No. 0252515). These known processes are either technically very expensive or the yields leave a great deal to be desired.

Another known process is described in J. Org Chem., 40, (1975), 3304. The key product used there is cyanoacetylpiperidinic acid amide, whose carboxyl group must first be made reactive. The materials necessary for this process are not easily available and ar linked to high expense.

Broad Description Of The Invention

The object of the invention is to provide a technically or industrially and economically feasible process for the production of Minoxidil, in good yield and great purity, with the elimination of the drawbacks of the above-described known processes. The object of the invention is achieved surprisingly by the process and intermediate compound of the invention.

The invention includes a process for the production of 2,4-diamino-6-piperidinyl-pyrimidine-3-N-oxide. In the process, hydroxylamine and cyanamide in a lower alcohol as a solvent in the presence of an alkali alcoholate are converted in situ into the corresponding hydroxyguanidine. The latter is converted with a cyanoacetic acid ester, with ring formation, to the 2,4-diamino-6-hydroxypyrimidine-3-Noxide. The N-oxide is chlorinated by chlorination with POCl₃ in the presence of an amine as the catalyst to 2,4-diamino-6-chloropyrimidine-3-N-oxide. The latter is converted with piperidine to the desired end product.

Preferably the hydroxyguanidine, starting from an aqueous cyanamide solution, is reacted with an aqueous hydrohalic acid to the corresponding haloformamidinium halide and the latter is converted with hydroxylamine in the presence of an alkali alcoholate in a lower alcohol to the corresponding hydroxyguanidine. Preferably hydrochloric acid is used as the aqueous hydrohalic acid. Preferably the hydroxylamine is used in hydrochloride form. Preferably methanol is used as the lower alcohol and sodium methylate is used as the alkali alcoholate. Preferably tertiary amines, most preferably N,N-dimethylaniline, are used as the catalyst for the reaction with POCl₃. Preferably the 2,4-diamino-6-hydroxypyrimidine-3-N-oxide is isolated before the next step. Also, preferably the 2,4-diamino-6-chloropyrimidine-3-N-oxide is isolated before the next step.

The invention also includes 2,4-diamino-6-hydroxypyrimidine-3-N-oxide. Such intermediate product is new and can occur as the hydrate or in the form of its salts.

Detailed Description Of The Invention

Minoxidil or the compounds occurring in the process according to the invention are subject to tautomerism, i.e., 2,4-diamino-6-piperidinyl-pyrimidine-3-N-oxide is in a tautomeric equilibrium with 6-amino-1,2-dihydro-1-hydroxy-2-imino-4-piperidinylpyrimidine. imino-4-piperidinylpyrimidine. For simplicity's sake, only the N-oxide form of the compounds is mentioned in the following embodiments. A preferred embodiment of the invention consists in the fact that the in situ formation of the hydroxyguanidine takes place by reaction of the hydroxylamine, preferably in the form of the hydrochloride, with cyanamide in methanol in the presence of sodium methylate. The educts as well as the sodium methylate are suitably used in molar ratio. The reaction time is suitably 2 to 4 hours and the preferred temperature is 0° to 20° C. Besides methanol, other lower alcohols, such as, ethanol n-propanol, and other alkali alcoholates, such as, sodium ethylate and sodium n-propylate, can be used. Then the formed sodium chloride is suitably filtered off.

Another process for achieving hydroxyguanidine involves converting, in a first stage, an aqueous cyanamide solution with an aqueous hydrogen halide solution to the corresponding haloformamidinium halide, isolating the latter and (as described above) converting this intermediate product hydroxylamine in the presence of an alkali alcoholate in a lower alcohol to hydroxyguanidine. The method to produce the haloformamidinium halide is disclosed in German OS 1,915,668.

Preferably the chloroformamidinium chloride is produced by reaction of an aqueous cyanamide solution with an aqueous hydrochloric acid.

Then the cyanoacetic ester, preferably the methyl ester, suitably in molar ratio, and additional sodium methylate, dissolved in methanol, are added. The temperature during the addition is suitably kept at 0° to 5° C.

Then the reaction mixture is kept for 1 to 2 hours at a temperature of 10° to 20° C. and brought to reflux temperature. The retention time at reflux is suitably 4 to 6 hours.

The formed 2,4-diamino-6-hydroxypyrimidine-3-N-oxide is preferably anhydrous or isolated as a hydrate, and then is fed to the chlorination stage. The molar ratio of 2,4-diamino-6-hydroxypyrimidine-3-N-oxide to POCl3 to N,N-dimethylaniline, as the preferred catalyst, is 1 to 5 to 1 to 1 to 10 to 3. Besides the preferred N,N-dimethylaniline, other catalysts, such as, N,N-diethylaniline, triethylamine and tributylamine, can also be used. The reaction temperature is 70°0 to 100° C., preferably 80° to 85° C. The reaction time is 10 to 80 hours, preferably 10 to 20 hours.

Suitably the formed 2,4-diamino-6-chloropyrimidine-Noxide is isolated as the free compound or as, e.g., the hydrochloride, and then is fed to the reaction with piperidine. In this case, suitably 15 to 25 mol of piperidine is used per mol of chlorination product. The preferred temperature is 70° to 104° C. and the reaction time is 2 to 5 hours.

EXAMPLE 1

(a) Production of 2,4-diamino-6-hydoxypyrimidine-N-oxide hydrate 6.95 g of hydroxylaminohydrochloride (0.1 mol), 4.2 g of cyanamide (0.1 mol) and 15 g of methanol were combined at 0° C., and 5.4 g of sodium methylate (30 percent in methanol, 0.1 mol) was added during 3 hours. The sodium chloride precipitate was filtered off and 9.9 g of cyanoacetic acid methyl ester (0.1 mol) was added to the filtrate. Additional 5.4 g of sodium methylate (30 percent in methanol, 0.1 mol) was added at 0° to 5° C. The reaction mixture was stirred for 1 hour at 15° C. and then for 4 hours at reflux temperature. The methanol was removed under vacuum and 60 g of water was added. The mixture was adjusted to pH 4.5 at 40° C. with 20 percent hydrochloric acid solution and cooled to room temperature. The solid was filtered off, washed with water and dried at 50° C./20 torrs. 7.02 g of brown powder with a content of 86.5 percent (crude product) was obtained. The yield was 42.7 percent relative to the cyanamide. The melting point of the product was above 300° C. Elementary analysis for the hydrate was:

Cld: C 30.0%, H 5.0%; N 35.0%; Fnd: C 30.1%; H 5.0% N 34.4%

Spectroscopic analyses of the product was:
$^1$H-NMR (DMSO-d6):
5.15 (s, IH),
7.15 (bs, 2H),
7.4 (bs, 2H).
OH group combines with water peak
$^{13}$C-NMR (DMSO-d$^6$) 80.0–155.8–158.0–164.5.

(b) Production of 6-chloro-2,4-diaminopyridine-3-N-oxide 5.0 g of 2,4-diamino-6-hydroxypyrimidine-3-N-oxide hydrate (0.035 mol), 40 g of phosphoroxychloride (0 26 mol) and 4.25 g of N,N-dimethylaniline (0.0352 mol) were combined and stirred for 60 hours at 82 C. The excess phosphoroxychloride was distilled off under vacuum. 100 g of water was carefully added to the residue. After 1 hour at room temperature, the pH was adjusted to 9 with 25 percent sodium hydroxide solution, and the reaction mixture was cooled. The product was filtered off, washed with water and dried at 50° C./20 torrs. 4.36 g of product, which correspond to a yield of 77 percent, was obtained.

(c) Production of 2,4-diamino-6-piperidinyl-pyrimidine-3-Noxide (Minoxidil)

2.0 g of 6-chloro-2,4-diaminopyrimidine-3-N-oxide (0.0125 mol) and 20.g (0.23 mol) of piperidine were stirred for 2 hours at 101° C. The reaction mixture was cooled to room temperature. The solid was filtered off, washed with water and dried at 50° C./20 torrs. 2.15 g of white powder was obtained; the melting point was above 258° C.; and the yield was 83 percent. The product was spectroscopically identical with authentic Minoxidil. Spectroscopic analysis of the product was:

$^1$H-NMR (DMSO-d6);
1.52 (m, 6H),
3.39 (t, 4H),
5.39 (s, IH),
6.72 (bs, 4H)
IR (KBr) cm−1 3450, 3422, 3400, 3373, 3273, 1644, 1250, 1211, 1158, 1021.

EXAMPLE 2

(a) 2,4-Diamino-6-hydroxypyrimidine-3-oxide hydrate 10.4 g of hydroxylaminohydrochloride (0.15 mol), 4.2 g of cyanamide (0.1 mol) and 20 g of methanol were combined at 20° to 25° C. Then 27 g of sodium methylate (30 percent in methanol, 0.15 mol) was added in 15 minutes. After 45 minutes the sodium precipitate was filtered off. The filtrate was added to a mixture of 17.82 g of cyanoacetic acid methyl ester (0.18 mol) and 32.4 g of sodium methylate (30 percent in methanol, 0.18mol). The reaction mixture was stirred for 4 hours at 22° C. and then for 2 hours at reflux temperature. It was adjusted to a pH of 4.5 at 55° to 60° C. with 18 percent hydrochloric acid solution. The methanol was then removed under vacuum. After cooling to 10° to 15° C., the solid was filtered off, washed with water and dried at 50.C/20 torrs. 0 16 g of the title compound was obtained. The yield amounted to 65.3 percent relative to the cyanamide. The melting point of the product was above 300° C. Spectroscopic analysis of the product was:

IR (KBr) cm−1 3401, 3325, 3218, 3200, 3156, 1708, 1650, 1553, 1515, 1488, 1446, 1256, 1146, 992.
UV (EtOH)nm: 224, 277
Elementary analysis for the product was:
Cld: C 30.0%, H 5.0% N 35.0% (hydrate),
Fnd: C 30.2%, H 5.1%, N 34.9%, (b) 2,4-Diamino-6-chloropyrimidine-3-oxide hydrochloride 170.0 g of 2,4-diamino-6-hydroxy-3-oxide hydrate (1.1 mol) and 1283 g of phosphoroxychloride (8.4 mol) were combined. 215 g of N,N'-dimethylaniline (1.8 mol) was added to 72° C. in 30 minutes. The reaction mixture was stirred for 15 hours at reflux temperature. The excess phosphoroxychloride was distilled off under vacuum at 80° C. The residue was added during 20 minutes to 1400 g of water of 20.C. The resultant suspension was stirred for 2 hours at 5° C. and filtered. The product was washed with cold water and dried at 50° C./20 torrs. 177.3 g of the title compound, corresponding to a yield of 80-percent, was obtained The melting point of the product was 142° C. (decomp.).

Spectroscopic analysis of the product was:
$^1$H-NMR (DMSO-d6): 8.05 (bs, 4H), 6.17 (s, IH),
HCl combines with water peak
IR (KBr) cm−1 3374, 3296, 3210, 3171, 3094, 1677, 1627, 1567, 1375, 1296, 1205, 945.
UV (H20)nm: 228, 290

EXAMPLE 3

Production of 2,4-diamino-6-hydroxypyrimidine-3-oxide hydrate 11.5 g of chloroformamidinium hydrochloride (0.1 mol), produced according to the instructions of German OS 19 15 668, was dissolved in 20 g of methanol. Then 18 g of sodium methylate (30 percent in methanol, 0.1 mol) was added at 15° to 20° C. A solution of 3.3 g of hydroxylamine in 20 g of methanol was added at 15° C. and the reaction mixture was stirred for 3 hours at 15° to 20° C. 10 g of cyanoacetic acid methyl ester (0.1 mol) and then 18 g of sodium methylate (30 percent in methanol, 0.1 mol) were added and kept at reflux temperature for 2 hours. The mixture was adjusted to pH 4.5 at 55° to 60° C. with 18 percent hydrochloric acid solution. Then enough methanol was evaporated under vacuum so that the ability of the mixture to be stirred was assured. After cooling to 10° to 15° C. and stirring for 10 minutes the solid was filtered off. The solid was washed with water and dried at 50° C./20 torrs. 6.4 g of beige powder with a content of 47.6 percent (crude product) was obtained. The yield was 21 percent relative to the chloroformamidinium hydrochloride. The product was analytically identical with the product of Example 2(a).

What is claimed is:

1. Process for the production of 2,4-diamino-6-piperidinyl-pyrimidine-3-N-oxide, comprising converting in situ hydroxylamine and cyanamide in a lower alcohol as a solvent in the presence of an alkali alcoholate into the corresponding hydroxyguanidine, converting the latter with a cyanoacetic acid ester, with ring formation, to the 2,4-diamino-6-hydroxypyrimidine-3-N-oxide, chlorinating the N-oxide by chlorination with $POCl_3$ the presence of an amine as a catalyst to 2,4-diamino-6-chloropyrimidine-3-N-oxide, and converting the latter with piperidine to the end product.

2. Process according to claim 1 wherein the hydroxyguanidine, starting from an aqueous cyanamide solution, is reacted with an aqueous hydrohalic acid to the corresponding haloformamidinium halide and the latter is converted with hydroxylamine in the presence of an alkali alcoholate in a lower alcohol to the corresponding hydroxyguanidine.

3. Process according to claim 2 wherein hydrochloric acid is used as the aqueous hydrohalic acid.

4. Process according to claim 3 wherein the hydroxylamine is used in hydrochloride form.

5. Process according to claim 4 wherein methanol is used as the lower alcohol and sodium methylate is used as the alkali alcoholate.

6. Process according to claim 5 wherein a tertiary amine is used as the catalyst for the reaction with $POCl_3$.

7. Process according to claim 6 wherein the tertiary amine is N,N-dimethylaniline.

8. Process according to claim 6 wherein the 2,4-diamino6-hydroxypyrimidine-3-N-oxide is isolated before the chlorination.

9. Process according to claim 1 wherein hydroxylamine is used in hydrochloride form.

10. Process according to claim 1 wherein methanol is used as the lower alcohol and sodium methylate is used as the alkali alcoholate.

11. Process according to claim 1 wherein a tertiary amine is used as the catalyst for the reaction with $POCl_3$.

12. Process according to claim 1 wherein the tertiary amine is N,N-dimethylaniline.

13. Process according to claim 1 wherein 2,4-diamino-6-hydroxypyrimidine-3-N-oxide is isolated before the conversion.

14. 2,4-Diamino-6-hydroxypyrimidine-3-N-oxide.

* * * * *